United States Patent [19]
Scheiblich et al.

[11] Patent Number: 5,747,423
[45] Date of Patent: May 5, 1998

[54] HERBICIDAL 6-THIENYL AND 4-THIENYL PYRIMIDINES

[75] Inventors: Stefan Scheiblich; Thomas Maier, both of Mainz; Helmut Siegfried Baltruschat, Schweppenhausen, all of Germany; Joseph Luke Pont, Lawrenceville, N.J.

[73] Assignee: American Cyanamid Company, Parsippany, N.J.

[21] Appl. No.: 680,193

[22] Filed: Jul. 15, 1996

[51] Int. Cl.$^6$ .................. C07D 401/04; C07D 401/14; A01N 43/40; A01N 43/66

[52] U.S. Cl. .................. 504/251; 546/284; 504/230; 504/236; 504/237; 504/239; 504/242; 504/243; 504/250; 504/235; 544/238; 544/180; 544/212; 544/209; 544/198; 544/207; 544/333; 544/331; 544/327; 544/324; 544/318; 544/310; 544/300; 544/405

[58] Field of Search .................. 504/251, 230, 504/236, 237, 239, 242, 243, 250, 235; 546/284; 544/238, 180, 212, 207, 209, 198, 333, 331, 327, 324, 318, 310, 300, 405

[56] References Cited

PUBLICATIONS

Chemica Scripta, 26, pp. 305–309 (1986), Gronowitz et al., On the Synthesis of various Thienyl—and Selenienylpyrimidines.

*Primary Examiner*—John M. Ford
*Attorney, Agent, or Firm*—Gregory M. Hill

[57] ABSTRACT

The novel 6-thienyl pyridines and 4-thienyl pyrimidines of formula I:

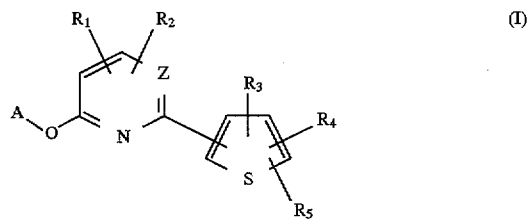

(A, $R_1$ to $R_5$ and Z are defined in the specification) show selective herbicidal activity.

The new compounds can be prepared according to known methods and can be used as herbicides in agriculture and related fields.

8 Claims, No Drawings

HERBICIDAL 6-THIENYL AND 4-THIENYL PYRIMIDINES

BACKGROUND OF THE INVENTION

Pyridines, pyrimidines and their derivatives have many uses in the pharmaceutical area as well as in agriculture (herbicides, fungicides, acaricides, anthelmintics, bird repellents), as reagents, intermediates and chemicals for the polymer and textile industry.

2-Arylpyrimidines and 2-pyrimidinyl-6-arylpyridines for example have been described as fungicides (DE 40 29 654 and JO 2131-480, respectively). EP 263,958 is concerned with herbicidal 2,6-diphenylpyridines, and structurally related 2,4-diphenylpyrimidines have been disclosed in EP 354,766 and EP 425,247, respectively, which are also said to be herbicides. Another example are 2,6-diphenoxypyridines, which have been published in EP 572,093 as herbicides. 4-Phenoxy-2-pyrazol-1-yl-pyrimidines are disclosed in DE 29 35 578 to have fungicidal activity. 2-thienylpyridines are known from EP 451585 and EP 693490. Huelsen (Diplomarbeit, Konstanz 1993) describes four distinct 2-(1-methyl-3-trifluoromethyl-pyrazol-5-ylyoxy)-6-phenyl pyridines, however, no biological activity is disclosed.

Although many of the known compounds show considerable activity against various weeds, they are not completely satisfying with regard to their selectivity or because of their persistence.

The compounds according to the present invention combine high herbicidal activity with the necessary selectivity and enhanced soil degradation.

SUMMARY OF THE INVENTION

The present invention provides novel 6-thienyl pyridines and 4-thienyl pyrimidines of formula I:

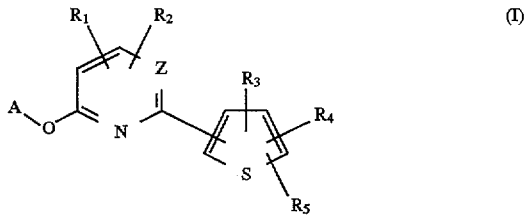

wherein
- A represents optionally substituted aryl group or an optionally substituted 5- or 6-membered nitrogen-containing heteroaromatic group or a difluorobenzodioxolyl group;
- $R_1$ and $R_2$ independently represent a hydrogen atom, a halogen atom, an optionally substituted alkyl, alkenyl, alkynyl, alkoxy, alkoxyalkyl, dialkoxyalkyl, alkoxyalkoxy, alkylthio, amino, alkylamino, dialkylamino, alkoxyamino or formamidino group;
- $R_3$, $R_4$ and $R_5$ independently represent a hydrogen atom, a halogen atom, an optionally substituted alkyl, alkenyl, alkynyl, alkoxy, haloalkyl, haloalkoxy, alkoxyalkoxy, alkylthio, haloalkylthio group or a nitro, cyano, $SF_5$ or a alkylsulphonyl or alkylsulfinyl group;
- Z represents a nitrogen atom or a $CR_6$ group; and
- $R_6$ represents a hydrogen or halogen atom, an optionally substituted alkyl, alkenyl, alkynyl, alkoxy, alkoxyalkoxy, alkylthio, cyano, amino, alkylamino, dialkylamino, alkoxyamino or formamidino group.

The new compounds show excellent selective herbicidal activity in certain crops, such as maize and rice, and exhibit enhanced soil degradation.

The invention also provides methods for controlling undesired plant growth by contacting said plants with a herbicidally effective amount of the new compounds.

It is another object of the invention to provide selective herbicidal compositions containing the new compounds as active ingredients.

Another object of the invention is to provide new processes for the preparation of the new compounds.

These and other objects and features of the invention will become more apparent from the detailed description set forth hereinbelow.

DETAILED DESCRIPTION OF THE INVENTION

Surprisingly, it has now been found that good herbicidal activity is present in novel 6-thienyl pyridines and 4-thienyl pyrimidines of formula I:

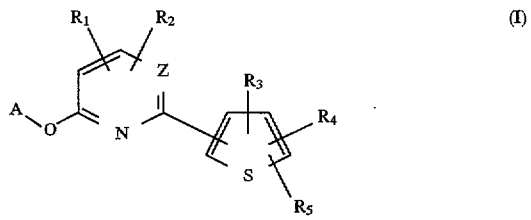

wherein
- A represents optionally substituted aryl group or an optionally substituted 5- or 6-membered nitrogen-containing heteroaromatic group or a difluorobenzodioxolyl group;
- $R_1$ and $R_2$ independently represent a hydrogen atom, a halogen atom, an optionally substituted alkyl, alkenyl, alkynyl, alkoxy, alkoxyalkyl, dialkoxyalkyl, alkoxyalkoxy, alkylthio, amino, alkylamino, dialkylamino, alkoxyamino or formamidino group;
- $R_3$, $R_4$ and $R_5$ independently represent a hydrogen atom, a halogen atom, an optionally substituted alkyl, alkenyl, alkynyl, haloalkyl, haloalkoxy, alkoxy, alkoxyalkoxy, alkylthio, haloalkylthio group or a nitro, cyano, $SF_5$ or a alkylsulphonyl or alkylsulfinyl group;
- Z represents a nitrogen atom or a $CR_6$ group and
- $R_6$ represents a hydrogen or halogen atom, an optionally substituted alkyl, alkenyl, alkynyl, alkoxy, alkoxyalkoxy, alkylthio, cyano, amino, alkylamino, dialkylamino, alkoxyamino or formamidino group.

These compounds unexpectedly show considerable activity and high selectivity in certain crops, such as maize and rice, in pre- and post-emergence applications on both broadleaf and grassy weed species, and also show enhanced soil degradation.

An aryl group as substituent or part of other substituents or in the definition of A is suitably an optionally substituted phenyl group. Within the definition of A the 5- or 6-membered heteroaryl group comprises optionally substituted 5- or 6-membered heterocycles containing one or more nitrogen and/or oxygen and/or sulfur atoms, 1 to 3 nitrogen atoms being preferred. Examples of such groups are pyrazolyl, imidazolyl, triazolyl, tetrazolyl, pyridyl, pyrazinyl, pyrimidyl, pyridazinyl, isoxazolyl, isothiazolyl and triazinyl groups. As far as A is concerned the definition "aryl" does also include bicyclic systems which consist of a benzene ring fused with a 5- or 6-membered heterocyclic ring as defined above and in turn the 5- or 6-membered heterocycles may be fused with a benzene ring. Another preferred embodiment of A is a difluorobenzodioxolyl group of formula

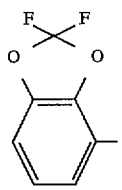

Generally, if any of the above mentioned moieties comprises an alkyl, alkenyl or alkynyl group, such groups, unless otherwise specified, may be linear or branched and may contain 1 to 6, preferably 1 to 4, carbon atoms. Examples of such groups are methyl, ethyl, propyl, vinyl, allyl, propargyl, isopropyl, butyl, isobutyl and tertiary-butyl groups. The alkyl portion of a haloalkyl, haloalkoxy, haloalkylthio, alkylthio or alkoxy group suitably has from 1 to 4 carbon atoms, preferably 1 or 2 carbon atoms. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine. Haloalkyl moieties of any groups within the definitions used herein and as such can contain one or more halogen atoms. Haloalkyl, haloalkoxy and haloalkylthio are preferably mono-, di- or trifluoroalkyl, -alkoxy and -alkylthio, especially trifluoromethyl, trifluoromethoxy, difluoromethoxy, difluoromethylthio, trifluoromethylthio or 2,2,2-trifluoroethoxy groups.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more of the same or different substituents present in each part of the molecules. In relation to moieties defined above as comprising an optionally substituted alkyl group, including alkyl parts of haloalkyl, alkoxy, alkylthio, haloalkoxy, alkylamino and dialkylamino groups, specific examples of such substituents include phenyl, halogen atoms, nitro, cyano, hydroxyl, $C_{1-4}$-alkoxy, $C_{1-4}$-haloalkoxy and $C_{1-4}$-alkoxycarbonyl groups.

In relation to moieties defined above as comprising an optionally substituted aryl or heteroaryl group, optional substituents include halogen, especially fluorine, chlorine and bromine atoms, and nitro, cyano, amino, hydroxyl, $C_{1-4}$-alkyl, $C_{1-4}$-alkoxy, $C_{1-4}$-haloalkyl, $C_{1-4}$-haloalkenyl, $C_{1-4}$-haloalkoxy, $C_{1-4}$-haloalkylthio and halosulfanyl groups such as $SF_5$. 1 to 5 substituents may suitably be employed, 1 to 2 substituents being preferred. Typically haloalkyl, haloalkoxy and haloalkylthio groups are trifluoromethyl, trifluoromethoxy, difluoromethoxy, trifluoroethoxy and trifluoromethylthio groups.

In formula I, A preferably represents a group of formula a, b or c:

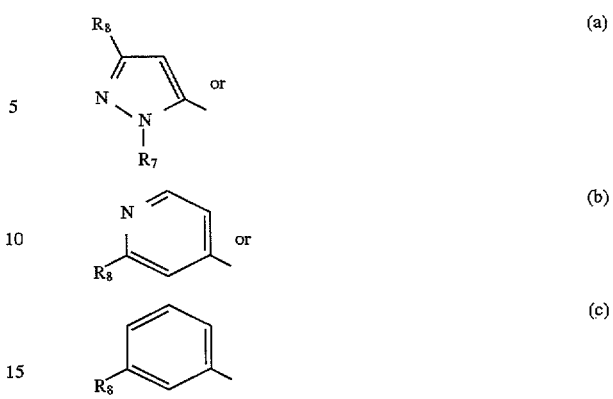

wherein $R_7$ is $C_{1-3}$ alkyl and $R_8$ is $C_{1-4}$ alkyl, $C_{1-3}$ haloalkyl, a halogen atom, $C_{1-3}$ haloalkoxy or $C_{1-3}$ haloalkylthio; while $R_1$ is methyl, ethyl, methoxy, fluorine, chlorine, methoxymethyl, $R_2$ is hydrogen, $R_3$ is $C_{1-4}$ alkyl, hydrogen, chlorine or trifluoromethyl and $R_4$ and $R_5$ are hydrogen and Z is nitrogen.

Particularly preferred are the compounds of formula Ia:

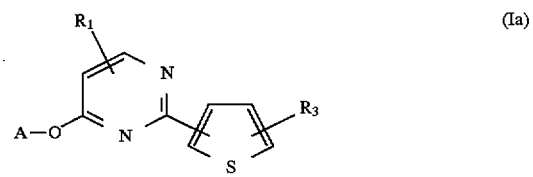

wherein
$R_1$ is 5-methyl, 6-methyl, 6-ethyl, 6-methoxy, 6-chloro, 6-methoxymethyl,
$R_3$ is 5-fluoro, 5-chloro or 5-trifluoromethyl,
A is selected from the groups:

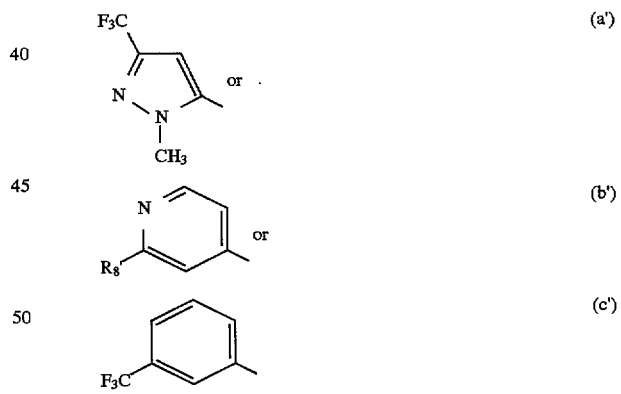

($R_8'$ is a chlorine atom, trifluoromethyl or difluoromethoxy).

The compounds according to general formula I possess a high herbicidal activity within a wide concentration range and may be used in agriculture or related fields for the selective control of undesired plants such as *Alopecurus myosuroides, Echinochloa crus-galli, Setaria viridis, Galium aparine, Stellaria media, Veronica persica, Lamium purpureum, Viola arvensis, Abutilon theophrasti, Ipomoea purpurea* and *Amaranthus retroflexus* by pre- and post-emergence application, particularly in certain crops, such as maize and rice.

The compounds according to the invention can be prepared by conventional methods, particularly as follows:

(A) A suitable process for the preparation of the compounds of general formula I comprises the reaction of a compound of formula II:

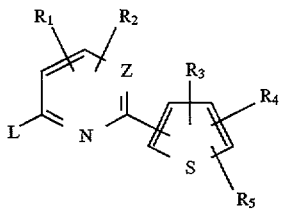

wherein

L represents a suitable leaving group and $R_1$ to $R_5$ and Z are as defined above, with a compound of formula III:

(wherein A is as defined hereinbefore), or a tautomer or a metal salt of III.

(B) Alternatively a compound of formula IV:

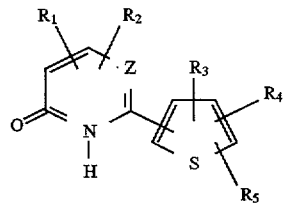

(wherein $R_1$ to $R_5$ and Z are as defined hereinbefore) or a tautomer thereof is coupled with a compound of formula V:

(wherein A and L are as defined herein before, A preferably being a pyridine ring).

The reactions according to (A) and (B) may be carried out in the absence or presence of a solvent which promotes the reaction or at least does not interfere with it. Preferred are polar, aprotic or protic solvents, suitably being N,N-dimethylformamide, dimethylsulfoxide, sulfolane, acetonitrile, methyl ethyl ketone, or an ether, such as tetrahydrofurane or dioxane, or alcoholes, or water, or mixtures thereof. The reaction is carried out at a temperature between ambient temperature and the reflux temperature of the reaction mixture, preferably at elevated temperature, especially at reflux temperature.

The reactions may be carried out in the presence of a basic compound such as an alkali hydroxide or carbonate, e.g. sodium or potassium hydroxide or carbonate, an alkali alkoxide, e.g. sodium ethoxide, or an organic base such as triethylamine.

A hydroxy compound used in the above reactions may be present in form of a salt, preferably as a salt of an alkali metal, particularly of sodium or potassium. Copper salt is most preferred.

Suitable leaving groups L are e.g. alkyl- and arylsulfonyl, alkyl- and arylsulfonyloxy, nitro and halogen, particularly fluorine, chlorine and bromine groups.

(C) Alternatively, a compound of formula VIII:

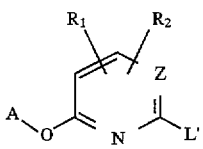

may be reacted with a derivative VI:

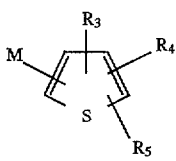

In formulae VII and VI the substituents $R_1$ to $R_5$ and A are as defined above.

M stands for Li, MgCl, MgBr, ZnCl, ZnBr, or B(OH)$_2$ or trialkyl tin. L' has independently the same meanings as L in formula II. If the reaction of VI and VII is followed by an oxidation step, L' can also be hydrogen, as for example described in J. Org. Chem. 53 (1988) 4137. The reaction of VI and VIII may be catalyzed by a transiton metal catalyst known in the art, the transition metal preferably being Pd or Ni, as for example described in Tetrahedron 48 (1992) 8117, and Chem. Scr. 26 (1986) 305.

The compounds used as starting material are known or can be prepared according to known methods.

Intermediates of formula II can be prepared from compounds IV by conventional methods known in pyrimidine and pyridine chemistry, as described in: G. R. Newkome, "Pyridine and its Derivatives", in The Chemistry of Heterocyclic Compounds, Vol. 14, Part 5, (1984); and D. J. Brown "The Pyrimidines", in The Chemistry of Heterocyclic Compounds, Vol. 52, (1994). If L represents a halogen atom, II can for example be prepared from IV by reaction with a halogenating agent like POCl$_3$, POBr$_3$, PCl$_5$, COCl$_2$, SO$_2$Cl$_2$, SOCl$_2$. Compounds II may also be prepared by reaction of a derivative VI with a pyridine or pyrimidine of formula VII:

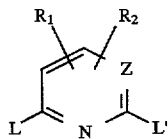

In formulae VI and VII the substituents $R_1$ to $R_5$ and M are as defined above.

L' has independently the same meanings as L. If the reaction of VI and VII is followed by an oxidation step, L' can also be hydrogen, as for example described in J. Org. Chem. 53 (1988) 4137. The reaction of VI and VII may be catalyzed by a transiton metal catalyst known in the art, the transition metal preferably being Pd or Ni, as for example described in Tetrahedron 48 (1992) 8117, and Chem. Scr. 26 (1986) 305.

For compounds of formula II, certain substituents $R_1$ like alkoxy, alkylthio, alkylamino, or fluorine, can be introduced onto the pyridine or pyrimidine ring by displacement of a chlorine or bromine atom by a compound $R_1$—H in the presence of a base, particularly if $R_1$ is at position 4 of the pyridine or 6 of the pyrimidine ring. Fluorine may also be introduced by diazotization.

The pyridones and pyrimidones of formula IV can be prepared by conventional methods commonly used for the formation of pyridinones and pyrimidones, as described in:

G. R. Newkome, "Pyridine and its Derivatives", in The Chemistry of Heterocyclic Compounds, Vol. 14, Part 5, (1984); and: D. J. Brown "The Pyrimidines", in The Chemistry of Heterocyclic Compounds, Vol. 52, (1994). Preferably, a thiophene carboxylic acid derivative is condensed with a β-ketocarboxylic acid derivative, like the well know reaction of an amidine with a β-ketoester in the presence of a base.

Intermediates of formula VIII can be prepared from intermediates of formula VII and compounds A—OH (III) analogously to the reaction between compounds II and III, described above.

The present invention also provides the use of the compounds of formula I as herbicides. Further, in accordance with the invention there is provided a method of combating undesired plant growth at a locus by treating the locus with a composition according to the invention or an effective amount of a compound of formula I. Foliar spray application, is most useful in such situations. Typical crops are cereals, maize, soya bean, sunflower or cotton. However, application may also be to the soil for those compounds having pre-emergence herbicidal action, or to the water of paddy rice fields. The dosage of active ingredient used may, for example be in the range of from 0.005 to 3 kg/ha, preferably 0.01 to 1 kg/ha.

The present invention also extends to a method of making a herbicidal composition of the invention which comprises blending a compound of formula I with at least one carrier.

Preferably there are at least two carriers in a composition of the present invention, at least one of which is a surface-active agent.

A carrier in a composition according to the invention is any material with which the active ingredient is formulated to facilitate application to the locus to be treated, which may be, as appropriate, a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicates such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumaron resins, polyvinyl chloride, and styrene polymers and copolymers; solid polychlorophenols; bitumen; waxes; solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; amides, for example DMF, aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface active agent. For example, the composition may contain at least two carriers, at least one of which is a surface-active agent.

A surface-active agent may be an emulsifying agent, a dispersing agent or a wetting agent; it may be non-ionic or ionic. Examples of suitable surface-active agents include the sodium or calcium salts of polyacrylic acids and lignin sulphonic acids, the condensation products of fatty acids or aliphatic amines or amides containing at least 12 carbon atoms in the molecule with ethylene oxide and/or propylene oxide, fatty acid esters of glycerol, sorbitol, sucrose or pentaerythrol, condensates of these with ethylene oxide and/or propylene oxide, condensation products of fatty alcohol or alkyl phenols, for example p-octylphenol or p-octylcresol, with ethylene oxide and/or propylene oxide, sulphates or sulphonates of these condensation products, alkali or earth alkali metal salts, preferably sodium salts, or sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate, and polymers of ethylene oxide and copolymers of ethylene oxide and propylene oxide.

The herbicidal composition of the invention may also contain other active ingredients, for example, compounds possessing insecticidal or fungicidal properties, or other herbicides.

A formulation containing a compound according to the invention can consist of 100 g of active ingredient (compound of formula I), 30 g of disperging agent, 3 g of antifoaming agent, 2 g of structure agent, 50 g of antifreezing agent, 0.5 g of a biocidal agent and water ad 1000 mL. Prior to use it is diluted with water to give the desired concentration of active ingredient.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

The structures of the compounds prepared in the following examples were additionally confirmed by NMR and mass spectrometry.

Preparation of Intermediates (a) 2-(5-Chloro-2-thienyl)-5-methyl-4-pyrimidone 2.0 g 5-Chlorothiophene-2-carboxamidine hydrochloride and 1.7 g methyl 2-formylpropionate are added to a 25% solution of potassium methoxide in methanol containing 6.2 g of KOMe. The mixture is stirred for 6 days, then the methanol is evaporated and the residue dissolved in water. Upon addition of hydrochloric acid the product precipitates as a white solid (m.p.>250° C.).

(b) 2-(5-Chloro-2-thienyl)-4-chloro 5-methylpyrimidine

The product of example 1 (1.6 g ) is dispersed in 15 mL $POCl_3$ and the mixture heated to 100° C. for 3 hours, and further stirred at room temperature over night. Careful hydrolysis with water yields a precipitate which is filtered, dissolved in ethyl acetate and washed with water. Drying and evaporation gives 1.65 g product (m.p. 137° C.).

(c) 4-Chloro-6-methoxy-2-(5-trifluoromethyl-2-thienyl) pyrimidine 2.05 g 2-Trifluoromethylthiophene in 20 mL diethylether are treated with 8.2 mL of a 1.6 M solution of n-butyllithium in hexane at −70° C. After 30 minutes the mixture is warmed to −40° C. and added dropwise to a solution of 2,4-dichloro-6-methoxypyrimidine in 20 mL of ether, which is kept at 0° C. The mixture is allowed to reach room temperature, is washed with water and 0.24 g of the product are isolated as an oil after flash chromatography.

(d) 2-Chloro-6-methyl-4-(1-methyl-3-trifluoromethyl-5-pyrazolyloxy)pyrimidine 5 g 2,4-Dichloro-6-methylpyrimidine, 5.3 g 1-methyl-3-trifluoromethyl-2-pyrazolin-5-one, and 6.2 g potassium carbonate in 100 mL dry acetonitrile are refluxed for 2 hours. The mixture is poured into water, extracted with ethyl acetate and chromatographed to give 6.1 g of the title compound (m.p. 65° C.).

The compounds listed in Tables A and C can be prepared in a similar manner.

The compounds in Table B can be prepared in a manner similar to the preparation of compounds of formula I, example 2.

TABLE A

Starting material of formula IIa:

(IIa)

| Compound No. | $R_1$ | thiophene bond at position | $R_3$ | m.p. [°C.] |
|---|---|---|---|---|
| 1 | 6-methoxy | 2 | 5-chloro | 74–75 |
| 2 | 6-chloro | 2 | 5-chloro | 105–108 |
| 3 | 6-methyl | 2 | 5-chloro | 66–68 |
| 4 | 6-methyl | 3 | 5-chloro | 92–97 |
| 5 | 5-methyl | 2 | 5-chloro | 137 |
| 6 | 6-methoxy | 2 | 5-$CF_3$ | oil |

TABLE B

Starting material of Formula IIb:

(IIb)

| Compound No. | $R_1$ | thiophene bond at position | $R_3$ | m.p. [°C.] |
|---|---|---|---|---|
| 1 | 4-methyl | 2 | 5-chloro | 52–55 |

TABLE C

Starting material of formula IVa:

(IVa)

| Compound No. | $R_1$ | thiophene bond at position | $R_3$ | m.p. [°C.] |
|---|---|---|---|---|
| 1 | 6-methyl | 2 | 5-chloro | 266–269 |
| 2 | 6-hydroxy | 2 | 5-chloro | >250 |
| 3 | 6-methyl | 3 | 5-chloro | >200 |

Preparation of Compounds of Formula I

Example 1

2-(5-Chloro-2-thienyl)4-chloro-6-(2-chloro-4-pyridyloxy)pyrimidine 0.4 g 2-(5-Chloro-2-thienyl)-4,6-dichloropyrimidine, 0.2 g 2-Chloro-4-hydroxypyridine, and 0.3 g potassium carbonate are refluxed in 30 mL dry acetonitril for 16 hours. The mixture is poured into water, and the product is extracted with toluene and purified by flash chromatography (0.38 g, m.p. 154°–156° C.).

Example 2

2-(3-thienyl)-6-methyl-4-(1-methyl-3-trifluoromethyl-5-pyrazolyloxy)-pyrimidine 0.145 g of 1,4-bis(diphenylphosphino)butane and 0.115 g bis(benzonitrile)palladium(II)chloride are refluxed in 10 m toluene under nitrogen for 2 hours. At room temperature 1 g 2-chloro-6-methyl-4-(1-methyl-3-trifluoromethyl-5-pyrazolyloxy)pyrimidine, 0.55 g thiophene-3-boronic acid, 0.8 g sodium hydrogen carbonate, 15 mL water and 20 mL dioxane are added, and the mixture is heated to reflux. After 2 hours another 0.2 g thiophene-3-boronic acid are added, and reflux continued for 1 hour. The organic phase is washed with with water and chromatographed to give 1 g of the title compound (m.p. 122° C.).

The compounds listed in the following tables can be prepared analogously to the examples and the methods described hereinbefore.

TABLE 1

Compounds of formula Ia:

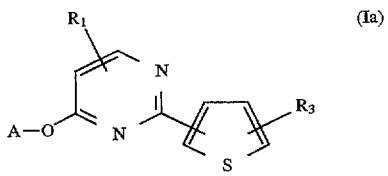

| Compound No. | $R_1$ | A | thiophene bond at position | $R_3$ | m.p. [°C.] |
|---|---|---|---|---|---|
| 1 | 6-methoxy | 3-$CF_3$-phenyl | 2 | 5-chloro | 55–58 |
| 2 | 6-methoxy | 1-$CH_3$-3-$CF_3$-pyrazol-5-yl | 2 | 5-chloro | 133–136 |
| 3 | 6-methoxy | 2-chloropyrid-4-yl | 2 | 5-chloro | 158–161 |
| 4 | 6-methoxy | 1-$CH_3$-3-$CF_3$-pyrazol-5-yl | 2 | 5-$CF_3$ | 102–106 |
| 5 | 5-methyl | 3-$CF_3$-phenyl | 2 | 5-chloro | 83 |
| 6 | 5-methyl | 1-$CH_3$-3-$CF_3$-pyrazol-5-yl | 2 | 5-chloro | 115 |
| 7 | 5-methyl | 2-chloropyrid-4-yl | 2 | 5-chloro | 120 |
| 8 | 6-methyl | 3-$CF_3$-phenyl | 2 | 5-chloro | 66–68 |
| 9 | 6-methyl | 1-$CH_3$-3-$CF_3$-pyrazol-5-yl | 2 | 5-chloro | 92–94 |
| 10 | 6-methyl | 2-chloropyrid-4-yl | 2 | 5-chloro | 132–135 |
| 11 | 6-chloro | 3-$CF_3$-phenyl | 2 | 5-chloro | oil |
| 12 | 6-chloro | 1-$CH_3$-3-$CF_3$-pyrazol-5-yl | 2 | 5-chloro | 114–117 |
| 13 | 6-chloro | 2-chloropyrid-4-yl | 2 | 5-chloro | 154–156 |
| 14 | 6-chloro | 1-$CH_3$-3-$CF_3$-pyrazol-5-yl | 2 | 5-$CF_3$ | |
| 15 | 6-methyl | 1-$CH_3$-3-$CF_3$-pyrazol-5-yl | 2 | 5-$CF_3$ | 102–106 |
| 16 | 6-methyl | 1-$CH_3$-3-$CF_3$-pyrazol-5-yl | 3 | 5-chloro | 92–95 |
| 17 | 5-methyl | 1-$CH_3$-3-$CF_3$-pyrazol-5-yl | 3 | 5-chloro | |
| 18 | 5-methyl | 2-$CF_3$-pyridyl-4-yl | 2 | 5-$CF_3$ | |
| 19 | 6-methyl | 2-$CF_3$-pyridyl-4-yl | 2 | 5-$CF_3$ | |
| 20 | 6-methoxy | 2-$CF_3$-pyridyl-4-yl | 2 | 5-$CF_3$ | |
| 21 | 6-methoxy | 2-$CF_3$-pyridyl-4-yl | 2 | 5-chloro | |
| 22 | 5-methyl | 2-$CHF_2O$-pyridyl-4-yl | 2 | 5-$CF_3$ | |
| 23 | 6-methyl | 2-$CHF_2O$-pyridyl-4-yl | 2 | 5-$CF_3$ | |
| 24 | 6-methoxy | 2-$CHF_2O$-pyridyl-4-yl | 2 | 5-$CF_3$ | |
| 25 | 6-methoxy | 2-$CHF_2O$-pyridyl-4-yl | 2 | 5-chloro | |
| 26 | 6-methoxy | 1-$CH_3$-3-$CF_3$-pyrazol-5-yl | 3 | 5-chloro | |

TABLE 2

Compounds of formula Ib:

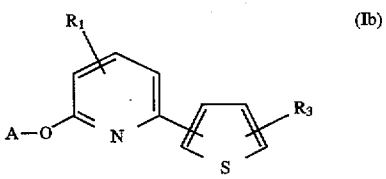

| Compound No. | $R_1$ | A | thiophene bond at position | $R_3$ | m.p. [°C.] |
|---|---|---|---|---|---|
| 1 | 4-methyl | 3-$CF_3$-phenyl | 2 | 5-chloro | |
| 2 | 4-methyl | 1-$CH_3$-3-$CF_3$-pyrazol-5-yl | 2 | 5-$CF_3$ | |
| 3 | 4-methyl | 3-$CF_3$-phenyl | 2 | 5-$CF_3$ | |
| 4 | 4-methoxy | 1-$CH_3$-3-$CF_3$-pyrazol-5-yl | 2 | 5-$CF_3$ | |
| 5 | 4-methoxy | 3-$CF_3$-phenyl | 2 | 5-chloro | |
| 6 | 4-methoxy | 3-$CF_3$-phenyl | 2 | 5-$CF_3$ | |
| 7 | 4-methyl | 1-$CH_3$-3-$CF_3$-pyrazol-5-yl | 2 | 5-chloro | 96–98 |

Pre-emergence Herbicidal Evaluation of Test Compounds

The pre-emergence herbicidal activity of the compounds of the present invention is exemplified by the following test in which the seeds of a variety of monocotyledonous and dicotyledonous plants are seperately mixed with potting soil and planted on top of approximately one inch of soil in separate pots. After planting the pots are sprayed with the selected aqueous acetone solution containing test compound in sufficient quantity to provide the equivalent of about 0.025 to 0.4 kg per hectare of test compound per pot. The treated pots are then placed on greenhouse benches, watered and cared for in accordance with conventional greenhouse procedures. At 2 to 4 weeks after treatment, the tests are terminated and each pot is examined and rated according to the system set forth above.

The herbicidal proficiency of the active ingredients of the present invention is evident from the test results which are recorded in Tables A, C and E below. The compounds of the invention displayed good herbicidal activity against dicotyledonous weed species. They were more selective in maize, soybeans, cereals, rice and other crops. Furthermore, they exhibited excellent activity on Setaria viridis, which in turn is one of the most important monocotyledonous species in maize.

| Rating System | % Difference in Growth from the check |
|---|---|
| 0-No effect | 0 |
| 1-Trace effect | 1–5 |
| 2-Slight effect | 6–15 |
| 3-Moderate effect | 16–29 |
| 4-Injury | 30–44 |
| 5-Definite injury | 45–64 |
| 6-Herbicidal effect | 65–79 |
| 7-Good herbicidal effect | 80–90 |
| 8-Aproaching complete kill | 91–99 |
| 9-Complete kill | 100 |

| Plant Species Used | | |
|---|---|---|
| TRZAW | Triticum aestivum | winter wheat |
| HORVW | Hordeum vulgare | winter barley |
| ZEAMX | Zea mays | maize |
| ORYSA | Oryza sativum | rice |
| GLYMA | Glycine max | soyabeans |
| GOSHI | Gossypium hirsutum | cotton |
| BEAVA | Beta vulgaris | sugar beets |
| BRSNW | Brassica napus | oil seed rape |
| ALOMY | Alopecurus myosuroides | blackgrass |
| AGRRE | Elytrigia repens | quackgrass |
| AVEFA | Avena fatua | wild oats |
| BROTE | Bromus tectorum | downy brome |
| CYPES | Cyperus eslulentus | yellow nutsedge |
| ECHGG | Echinichloa crus-galli | barnyardgrass |
| LOLMU | Lolium multiflorum | ryegrass |
| SETVI | Setaria viridis | green foxtail |
| SORHA | Sorghum halapense | johnsongrass |

-continued

| Plant Species Used | | |
|---|---|---|
| ABUTH | Abutilon theophrasti | velvetlaef |
| AMBEL | Ambrosia artemisiifolia | ragweed |
| BIDPI | Bidens pilosa | beggarticks |
| GALAP | Galium aparine | cleaver |
| IPOHE | Ipomoea hederacea | morning glory |
| LAMPU | Lamium purpureum | purple deadnettle |
| MATIN | Matricaria inodora | mayweed |
| PAPRH | Papaver rhoeas | poppy |
| VERPE | Veronica persica | speedwell |
| STEME | Stellaria media | chickweed |
| CASOB | Senna obtusifolia | sicklepod |
| EPHHL | Euphorbia heterophylla | poinsettia |
| SEBEX | Sesbania exaltata | hemb sesbania |

Post-emergence Herbicidal Evaluation of Test Compounds

The post-emergence herbicidal activity of the compounds of the present invention is demonstrated by the following test, wherein a variety of monocotyledonous and dicotyledonous plants are treated with formulations prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels equivalent of about 0.025 to 0.4 kg per hectare of test compound per pot. After spraying the plants are placed on greenhouse benches and are cared for in the usual manner, commensurate with conventional greenhouse practices. At 2 to 4 weeks after treatment, the seedling plants are examinated and rated according to the rating system provided below. A rating 0 indicates growth as untreated check, a rating 9 indicates death. The results of the tests are set out in Tables B, D and F below. The compounds of the invention showed good performance on monocotyledonous and dicotyledonous weeds and good tolerance in maize and cereals.

The compounds of the invention showed good selectivity in different crops such as wheat, barley, maize, rice, soybeans and cotton. This is shown in Table A.

TABLE A

| Phytotoxicity-tolerance in various crops - pre-emergence application | | | | | | | | | |
|---|---|---|---|---|---|---|---|---|---|
| Compound | Dose/kg/ha | TRZAW | HORVW | ZEAMX | ORYSA | GLXMA | GOSHI | BEAVA | BRSNW |
| Tab. 1/no. 1 | 0.4 | 0 | 2 | 0 | 0 | 0 | x | x | x |
|  | 0.1 | 0 | 0 | 0 | 0 | 0 | 0 | 0 | 2 |
|  | 0.025 | 0 | 0 | 0 | 0 | 0 | x | x | x |
| Tab. 1/no. 2 | 0.4 | 2 | 4 | 3 | 3 | 3 | x | x | x |
|  | 0.1 | 2 | 3 | 3 | 2 | 1 | 2 | 2 | 6 |
|  | 0.025 | 0 | 2 | 1 | 1 | 0 | x | x | x |
| Tab. 1/no. 6 | 0.4 | 2 | 4 | 4 | 2 | 3 | x | x | x |
|  | 0.1 | 1 | 2 | 2 | 1 | 2 | 0 | 7 | 7 |
|  | 0.025 | 0 | 1 | x | 0 | 1 | x | x | x |
| Tab. 1/no. 5 | 0.4 | 2 | 4 | 4 | 1 | 2 | x | x | x |
|  | 0.1 | 1 | 3 | 1 | 1 | 1 | 0 | 7 | 8 |
|  | 0.025 | 0 | 1 | 1 | 0 | 0 | x | x | x |
| Tab. 1/no. 9 | 0.4 | 0 | 2 | 2 | 0 | 2 | x | x | x |
|  | 0.1 | 0 | 1 | 1 | 0 | 1 | 0 | 5 | 6 |
|  | 0.025 | 0 | 0 | 0 | 0 | 1 | x | x | x |
| Tab. 1/no. 8 | 0.4 | 0 | 1 | 1 | 0 | 0 | x | x | x |
|  | 0.1 | 0 | 0 | 0 | 0 | 0 | 0 | 2 | 3 |
|  | 0.025 | 0 | 0 | 0 | 0 | 0 | x | x | x |
| Tab. 1/no. 12 | 0.4 | 0 | 0 | 1 | 1 | 0 | x | x | x |
|  | 0.1 | 0 | 0 | 0 | 0 | 0 | 0 | 3 | 4 |

TABLE A-continued

| Phytotoxicity-tolerance in various crops - pre-emergence application | | | | | | | | | |
|---|---|---|---|---|---|---|---|---|---|
| Compound | Dose/kg/ha | TRZAW | HORVW | ZEAMX | ORYSA | GLXMA | GOSHI | BEAVA | BRSNW |
| | 0.025 | 0 | 0 | 0 | 0 | 0 | x | x | x |
| Tab. 1/no. 11 | 0.4 | 0 | 0 | 1 | 0 | 0 | x | x | x |
| | 0.1 | 0 | 0 | 0 | 0 | 0 | 0 | 1 | 2 |
| | 0.025 | 0 | 0 | 0 | 0 | 0 | x | x | x |

The compounds of the invention, in particular Tab.1/no.2, Tab.1/no.9, Tab.1/no.8, Tab.1/no.12 and Tab.1/no.11 displayed good selectivity in cereals. At low doses in particular Tab.1/no.1, Tab.1/no.2, Tab.1/no.8 and Tab.1/no.11 showed good tolerance in maize. Excellent rice tolerance was recorded for Tab.1/no.1, Tab.1/no.2, Tab.1/no.8, Tab.1/no.12 and Tab.1/no.11.

TABLE B

| Phytotoxicity-tolerance in various crops - post-emergence application | | | | | | |
|---|---|---|---|---|---|---|
| Compound | Dose/kg/ha | TRZAW | HORVW | ZEAMX | ORYSA | GOSHI |
| Tab. 1/no. 1 | 0.4 | 2 | 3 | 4 | 2 | x |
| | 0.1 | 2 | 3 | 2 | 2 | 3 |
| | 0.025 | 1 | 2 | 2 | 1 | x |
| Tab. 1/no. 2 | 0.4 | 2 | 3 | 4 | 2 | x |
| | 0.1 | 0 | 3 | 3 | 2 | 4 |
| | 0.025 | 0 | 2 | 2 | 0 | x |
| Tab. 1/no. 4 | 0.4 | 4 | 5 | 4 | 4 | x |
| | 0.1 | 3 | 5 | 4 | 3 | 4 |
| | 0.025 | 1 | 4 | 3 | 1 | x |
| Tab. 1/no. 6 | 0.4 | 2 | 4 | 4 | 3 | x |
| | 0.1 | 1 | 3 | 4 | 2 | 0 |
| | 0.025 | 1 | 2 | 3 | 1 | x |
| Tab. 1/no. 9 | 0.4 | 3 | 4 | 4 | 4 | x |
| | 0.1 | 2 | 3 | 3 | 2 | 0 |
| | 0.025 | 1 | 2 | 3 | 1 | x |
| Tab. 1/no. 8 | 0.4 | 2 | 3 | 3 | 2 | x |
| | 0.1 | 1 | 2 | 2 | 1 | 0 |
| | 0.025 | 1 | 1 | 1 | 0 | x |
| Tab. 1/no. 12 | 0.4 | 2 | 2 | 4 | 1 | x |
| | 0.1 | 1 | 2 | 3 | 1 | 3 |
| | 0.025 | 1 | 1 | 2 | 1 | x |
| Tab. 1/no. 11 | 0.4 | 1 | 2 | 3 | 1 | x |
| | 0.1 | 1 | 2 | 2 | 1 | 4 |
| | 0.025 | 0 | 1 | 2 | 0 | x |

Table C: The compounds of the invention showed good activity on grasses, particularly on *Setaria*. Tab.1/no.2 and Tab.1/no.4 were also quite active on *Alopecurus*.

TABLE C

| Activity on grasses - pre-emergence application | | | | | | | | | |
|---|---|---|---|---|---|---|---|---|---|
| Compound | Dose/kg/ha | ALOMY | AGRRE | AVEFA | BROTE | ECHCG | LOLMU | SETVI | SORHA |
| Tab. 1/no. 1 | 0.4 | 5 | x | x | x | x | x | 8 | x |
| | 0.1 | 4 | 0 | 0 | 0 | x | 0 | 5 | 1 |
| | 0.025 | 2 | x | x | x | x | x | 4 | x |
| Tab. 1/no. 2 | 0.4 | 9 | x | x | x | x | x | 9 | x |
| | 0.1 | 8 | 5 | 4 | 5 | x | 5 | 9 | 5 |
| | 0.025 | 5 | x | x | x | x | x | 7 | x |
| Tab. 1/no. 4 | 0.4 | 9 | x | x | x | x | x | 9 | x |
| | 0.1 | 8 | 8 | 5 | 8 | x | 8 | 9 | 8 |
| | 0.025 | 7 | x | x | x | x | x | 9 | x |
| Tab. 1/no. 6 | 0.4 | 4 | x | x | x | x | x | 8 | x |
| | 0.1 | 3 | 5 | 2 | 0 | 1 | x | 7 | 7 |
| | 0.025 | 2 | x | x | x | x | x | 3 | x |

TABLE C-continued

Activity on grasses - pre-emergence application

| Compound | Dose/kg/ha | ALOMY | AGRRE | AVEFA | BROTE | ECHCG | LOLMU | SETVI | SORHA |
|---|---|---|---|---|---|---|---|---|---|
| Tab. 1/no. 5 | 0.4 | 8 | x | x | x | x | x | 9 | x |
| | 0.1 | 4 | 8 | 4 | 1 | 2 | x | 8 | 7 |
| | 0.025 | 2 | x | x | x | x | x | 4 | x |
| Tab. 1/no. 9 | 0.4 | 6 | x | x | x | x | x | 9 | x |
| | 0.1 | 2 | 5 | 1 | 0 | 1 | x | 8 | 3 |
| | 0.025 | 0 | x | x | x | x | x | 1 | x |

Table D: Performance of Tab.1/no.4, Tab.1/no.6, Tab.1/no.5 and Tab.1/no.9 performance on *Setaria* and at a dose of 400 g/ha also against *Alopecurus*.

TABLE D

Performance on grasses - post-emergence application

| Compound | Dose/kg/ha | ALOMY | AGRRE | AVEFA | BROTE | SETVI |
|---|---|---|---|---|---|---|
| Tab.1/no.4 | 0.4 | 8 | x | x | x | 8 |
| | 0.1 | 7 | 8 | 9 | 8 | 8 |
| | 0.025 | 4 | x | x | x | 5 |
| Tab.1/no.6 | 0.4 | 8 | x | x | x | 8 |
| | 0.1 | 5 | 5 | 4 | 5 | 8 |
| | 0.025 | 3 | x | x | x | 5 |

TABLE D-continued

Performance on grasses - post-emergence application

| Compound | Dose/kg/ha | ALOMY | AGRRE | AVEFA | BROTE | SETVI |
|---|---|---|---|---|---|---|
| Tab.1/no.5 | 0.4 | 9 | x | x | x | 9 |
| | 0.1 | 7 | 8 | 4 | 6 | 9 |
| | 0.025 | 3 | x | x | x | 6 |
| Tab.1/no.9 | 0.4 | 8 | x | x | x | 8 |
| | 0.1 | 4 | 4 | 3 | 4 | 8 |
| | 0.025 | 2 | x | x | x | 5 |

TABLE E

Performance on broad-leaf weeds - pre-emergence application

| Compound | Dose kg/ha | ABUTH | AMBEL | GALAP | IPOHE | LAMPU | MATIN | PAPRH | VERPE | STEME | CASOB |
|---|---|---|---|---|---|---|---|---|---|---|---|
| Tab. 1/no. 1 | 0.4 | 0 | x | 0 | 2 | x | 5 | x | 5 | x | x |
| | 0.1 | 0 | x | 0 | 1 | x | 4 | x | 4 | x | 0 |
| | 0.025 | 0 | x | 0 | 0 | x | 1 | x | 1 | x | x |
| Tab. 1/no. 2 | 0.4 | 3 | x | 1 | 7 | x | 8 | x | 9 | x | x |
| | 0.1 | 2 | x | 0 | 5 | x | 8 | x | 8 | x | 8 |
| | 0.025 | 1 | x | 0 | 3 | x | 5 | x | 7 | x | x |
| Tab. 1/no. 4 | 0.4 | 9 | x | 9 | 6 | 9 | 9 | 9 | 9 | x | x |
| | 0.1 | 7 | x | 4 | x | 8 | 9 | 9 | 9 | x | 8 |
| | 0.025 | 4 | x | 2 | 2 | 6 | 7 | 8 | 8 | x | x |
| Tab. 1/no. 6 | 0.4 | 4 | 9 | 3 | 3 | 9 | 9 | x | 9 | 9 | x |
| | 0.1 | 1 | 8 | 2 | 2 | 8 | 8 | x | 9 | 9 | 2 |
| | 0.025 | 1 | 3 | 0 | 1 | 8 | x | x | 5 | 4 | x |
| Tab. 1/no. 5 | 0.4 | 6 | 8 | 4 | 5 | 8 | 9 | x | 9 | 9 | x |
| | 0.1 | 2 | 8 | 1 | 2 | 7 | 8 | x | 8 | 9 | 1 |
| | 0.025 | 1 | 5 | 0 | 1 | 5 | 4 | x | 4 | 4 | x |
| Tab. 1/no. 9 | 0.4 | 2 | 9 | 2 | 3 | 9 | 9 | x | 9 | 9 | x |
| | 0.1 | 1 | 4 | 0 | 2 | 7 | 9 | x | 9 | 6 | 2 |
| | 0.025 | 0 | 2 | 0 | 1 | 2 | 4 | x | 1 | 3 | x |
| Tab. 1/no. 8 | 0.4 | 1 | 3 | 0 | 2 | 5 | 7 | x | 9 | 5 | x |
| | 0.1 | 0 | 2 | 0 | 1 | 2 | 4 | x | 3 | 2 | 0 |
| | 0.025 | 0 | 1 | 0 | 0 | 1 | 2 | x | 0 | 2 | x |
| Tab. 1/no. 12 | 0.4 | 0 | 8 | 1 | 2 | 6 | 9 | 6 | 7 | 2 | x |
| | 0.1 | 0 | 7 | 0 | 1 | 2 | 7 | 0 | 4 | 0 | 0 |
| | 0.025 | 0 | 2 | 0 | 0 | 0 | 0 | 0 | 0 | 0 | x |

The post-emergence activity of various compounds of the invention on broad-leaf weeds is shown in the next Table.

TABLE F

| | | Performance on broad-leaf weeds - post-emergence application | | | | | | | | | |
|---|---|---|---|---|---|---|---|---|---|---|---|
| Compound | Dose kg/ha | AMBEL | GALAP | IPOHE | LAMPU | MATIN | PAPRH | VERPE | STEME | CASOB | EPHHL |
| Tab. 1/no. 2 | 0.4 | x | 4 | 4 | x | 5 | x | 7 | x | x | x |
| | 0.1 | x | 3 | 3 | x | 3 | x | 6 | x | 5 | 5 |
| | 0.025 | x | 2 | 3 | x | 2 | x | 4 | x | x | x |
| Tab. 1/no. 4 | 0.4 | x | 8 | 9 | 8 | 8 | 9 | 9 | x | x | x |
| | 0.1 | x | 8 | 9 | 8 | 8 | 9 | 9 | x | 8 | 9 |
| | 0.025 | x | 6 | 9 | 8 | 7 | 9 | 8 | x | x | x |
| Tab. 1/no. 6 | 0.4 | 6 | x | 9 | 7 | 6 | 8 | 9 | 7 | x | x |
| | 0.1 | 5 | 4 | 9 | 6 | 4 | 7 | 9 | 5 | 6 | 9 |
| | 0.025 | 4 | x | 9 | 4 | 3 | 5 | 9 | 3 | x | x |
| Tab. 1/no. 5 | 0.4 | 6 | x | 9 | 8 | 7 | 8 | 9 | 6 | x | x |
| | 0.1 | 4 | 4 | 8 | 6 | 4 | 8 | 9 | 6 | 5 | 9 |
| | 0.025 | 4 | x | 5 | 4 | 3 | 6 | 8 | 3 | x | x |
| Tab. 1/no. 9 | 0.4 | 5 | x | 9 | 6 | 5 | 8 | 9 | 7 | x | x |
| | 0.1 | 4 | 3 | 9 | 4 | 4 | 8 | 9 | 5 | 4 | 9 |
| | 0.025 | 3 | x | 7 | 2 | 3 | 5 | 7 | 4 | x | x |
| Tab. 1/no. 8 | 0.4 | 4 | x | 6 | 3 | 4 | 7 | 8 | 3 | x | x |
| | 0.1 | 4 | 2 | 4 | 4 | 2 | 4 | 1 | x | 3 | 1 |
| | 0.025 | 4 | x | x | 3 | x | x | x | 2 | x | x |

What is claimed is:

1. A compound comprising 6-thienyl pyridines of formula I:

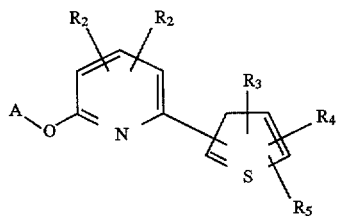

(I)

wherein

A represents an optional substituted phenyl group or an optionally substituted 5- or 6- membered nitrogen-containing heteroaromatic group selected from the group consisting of pyrazolyl, imidazolyl, triazolyl, tetrazolyl, pyridyl, pyrazinyl, pyrimidyl, pyridazinyl, isoxazolyl, isothiazolyl and triazinyl; in which the optional substituents include halogen atoms, and nitro, cyano, amino, hydroxyl, $C_{1-4}$ alkyl, $C_{1-4}$-alkoxy, $C_{1-4}$-haloalkyl, $C_{1-4}$ haloalkenyl, $C_{1-4}$ haloalkoxy, $C_{1-4}$-haloalkylthio and halosulfanyl groups;

$R_1$ and $R_2$ independently represents a hydrogen atom, a halogen atom, an optionally substituted alkyl, alkenyl, alkynyl, alkoxy, alkoxyalkyl, dialkoxyalkyl, alkoxyalkoxy, alkylthio, amino, alklamino, dialkylamino, or an alkoxyamino group;

in which the optional substituents are selected from the group consisting of phenyl, halogen atoms, nitro, cyano, hydroxyl, $C_{1-4}$-alkoxy, $C_{1-4}$ haloalkoxy and $C_{1-4}$-alkoxycarbonyl; and in which the moieties comprising an alkyl, alkenyl or alkynyl group contain 1 to 6 carbon atoms; or formamidino group;

$R_3$, $R_4$, and $R_5$ independently represents a hydrogen atom, a halogen atom, an optionally substituted alkyl, alkenyl, alkynyl, haloalkyl, haloalkoxy, alkoxy, alkoxyalkoxy, alkylthio, haloalkylthio alkylsulphonyl or alkylsulfinyl group;

in which the optional substituents are selected from phenyl, halogen atoms, nitro, cyano, hydroxyl, $C_{1-4}$ alkoxy, $C_{1-4}$-haloalkoxy and $C_{1-4}$-alkoxycarbonyl groups; and in which the moieties comprising an alkyl, alkenyl or alkynyl group contain 1 to 6 carbon atoms; or a nitro, cyano or $SF_5$ group.

2. The Compound as claimed in claim 1, wherein A represents a group of formula a, b or c:

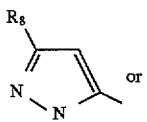

(a)

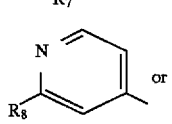

(b)

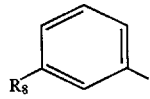

(c)

wherein $R_7$ is $C_{1-3}$ alkyl and $R_8$ is $C_{1-4}$ alkyl, $C_{1-3}$ haloalkyl, a halogen atom, $C_{1-3}$ haloalkylthio, $R_1$ is methyl, ethyl, methoxy, chlorine, methoxymethyl, $R_2$ is hydrogen, $R_3$ is $C_{1-4}$ alkyl, hydrogen, chlorine or trifluoromethyl and $R_4$ and $R_5$ are hydrogen.

3. Pyridines of formula 1b:

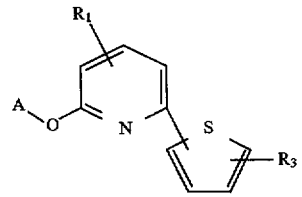

(1b)

wherein $R_1$, $R_3$ and A have the meaning given in claim 1.

4. Pyridines according the claim 3, wherein $R_1$ is attached to the pyridine group in the 4-position.

5. A compound selected from the group consisting of 6-(5-chloro-2-thienyl)-4-methyl-2-(3-trifluoromethylphenyloxy)pyridine, 6-(5-trifluoromethyl-2-thienyl)-4-methyl-2-(1-methyl-3-trifluoromethyl-5-pyrazolyloxy)pyridine, 6-(5-trifluoromethyl-2-thienyl)-4-methyl-2-(3-trifluoromethylphenyloxy)pyridine, 6-(5-trifluoromethyl-2-thienyl)-4-methoxy-2-(1-methyl-3-trifluoromethyl-5-pyrazolyloxy)pyridine, 6-(5-chloro-2-thienyl)-4-methoxy-2-(3-trifluoromethylphenyloxy)pyridine, 6-(5-trifluoromethyl-2-thienyl)-4-methoxy-2-(3-trifluoromethylphenyloxy)pyridine, and 6-(5-chloro-2-thienyl)-4-methyl-2-(1-methyl-3-trifluoromethyl-5-pyrazolyloxy)pyridine.

6. A herbicidal composition comprising compound as claimed in claim 1, carrier and/or auxiliaries and/or adjuvants.

7. A method for combating undesired plants, which method comprises treating a locus in need of such treatment with an effective amount of a compound as claimed in claim 1.

8. The method of claim 7 wherein the locus comprises crop plants selected from the group consisting of maize and rice.

* * * * *